(12) United States Patent
Robb et al.

(10) Patent No.: US 7,718,109 B2
(45) Date of Patent: May 18, 2010

(54) TISSUE SUPPORT STRUCTURE

(75) Inventors: Richard A. Robb, Rochester, MN (US); Srinivasan Rajagopalan, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1045 days.

(21) Appl. No.: 11/351,860

(22) Filed: Feb. 14, 2006

(65) Prior Publication Data

US 2006/0249875 A1 Nov. 9, 2006

Related U.S. Application Data

(60) Provisional application No. 60/652,924, filed on Feb. 14, 2005.

(51) Int. Cl.
*B29C 35/08* (2006.01)
*A61F 2/00* (2006.01)

(52) U.S. Cl. ............................. 264/308; 424/426
(58) Field of Classification Search ........... 264/308; 424/426

See application file for complete search history.

(56) References Cited

U.S. PATENT DOCUMENTS

| | | | |
|---|---|---|---|
| 5,490,962 A | 2/1996 | Cima et al. |
| 5,518,680 A | 5/1996 | Cima et al. |
| 5,869,170 A | 2/1999 | Cima et al. |
| 5,916,265 A | 6/1999 | Hu |
| 6,110,487 A | 8/2000 | Timmons et al. |
| 6,143,293 A | 11/2000 | Weiss et al. |
| 6,197,575 B1 | 3/2001 | Griffith et al. |
| 6,471,993 B1 | 10/2002 | Shastri et al. |
| 6,472,210 B1 | 10/2002 | Holy et al. |
| 6,530,958 B1 | 3/2003 | Cima et al. |
| 6,547,994 B1 | 4/2003 | Monkhouse et al. |
| 6,773,713 B2 | 8/2004 | Bonassar et al. |
| 6,828,357 B1 | 12/2004 | Martin et al. |
| 6,838,493 B2 | 1/2005 | Williams et al. |
| 6,867,247 B2 | 3/2005 | Williams et al. |
| 6,867,248 B1 | 3/2005 | Martin et al. |
| 6,872,387 B1 | 3/2005 | Ma |
| 2002/0102674 A1* | 8/2002 | Anderson ............... 435/174 |
| 2002/0182241 A1 | 12/2002 | Borenstein et al. |
| 2003/0114936 A1 | 6/2003 | Sherwood et al. |

(Continued)

OTHER PUBLICATIONS

B. Dhariwala, M.S., et al., "Rapid Prototyping of Tissue-Engineering Constructs, Using Photopolymerizable Hydrogels and Stereolithography," Tissue Engineering, vol. 10, No. 9/10, 2004, pp. 1316-1322.

(Continued)

*Primary Examiner*—Philip C Tucker
*Assistant Examiner*—Robert J Grun
(74) *Attorney, Agent, or Firm*—Fish & Richardson P.C.

(57) ABSTRACT

Techniques for generating tissue support structure are presented. A curved minimal surface shape is determined as a template for generating a tissue support structure. The determined curved minimal surface shape is numerically or functionally defined to create data representing the shape. The data is exported to a rapid prototyping system to generate a plurality of tissue support structures having a curved minimal surface. The tissue support structure can have a pore sub-section and a non-pore sub-section divided by a non-intersecting two-sided surface. A number of characteristics of the tissue support structure can be modulated including porosity and mechanical strength.

13 Claims, 11 Drawing Sheets

U.S. PATENT DOCUMENTS

| | | |
|---|---|---|
| 2003/0173695 A1 | 9/2003 | Monkhouse et al. |
| 2003/0175410 A1 | 9/2003 | Campbell et al. |
| 2004/0005297 A1 | 1/2004 | Connelly et al. |
| 2004/0254668 A1 | 12/2004 | Jang et al. |
| 2004/0258729 A1 | 12/2004 | Czernuszka et al. |

OTHER PUBLICATIONS

S. J. Hollister, "Porous Scaffold Design for Tissue Engineering," Nature Materials, vol. 4 Jul. 2005, pp. 518-524.

S. J. Hollister, "Engineering Craniofacial Scaffolds," Orthod Craniofacial, Res 8, 2005, pp. 162-173.

S. J. Hollister et al., "Optimal Design and Fabrication of Scaffolds to Mimic Tissue Properties and Satisfy Biological Constraints," Biomaterials 23, 2002, pp. 4095-4103.

D. W. Hutmacher et al., "Scaffold-Based Tissue Engineering: Rational for Computer-Aided Design and Solid Free-Form Fabrication Systems," TRENDS in Biotechnology, vol. 22, No. 7, Jul. 2004, pp. 354-362.

K. F. Leong et al., "Solid Freeform Fabrication of Three-Dimensional Scaffolds for Engineering Replacement Tissues and Organs," Biomaterials 24, 2003, pp. 2363-2378.

P. Quadrani et al., "High-Resolution 3D Scaffold Model for Engineered Tissue Fabrication Using a Rapid Prototyping Technique," Medical & Biological Engineering & Computing 2005, vol. 43, pp. 196-199.

T. D. Roy et al., "Performance of Degradable Composite Bone Repair Products Made Via Three-Dimensional Fabrication Techniques," J Biomed Mater Res 66A: 2003, pp. 283-291.

E. Sachlos et al., "Making Tissue Engineering Scaffolds Work. Review On The Application Of Solid Freeform Fabrication Technology To The Production Of Tissue Engineering Scaffolds," European Cells and Materials, vol. 5, 2003, pp. 29-40.

J.M. Taboas et al., "Indirect Solid Free Form Fabrication of Local and Global Porous, Biomimetic and Composite 3D Polymer-Ceramic Scaffolds," Biomaterials 24, 2003, pp. 181-194.

W. Sun et al, "Review Computer-Aided Tissue Engineering: Overview, Scope and Challenges," Biotechnol. Appl. Biochem, 2004, 39, 29-47.

Burke P. Robinson, MD et al., "Calvarial bone repair with porous $_{D,L}$-polylactide," *Experimental Studies (Isla Schwartz, PhD, Experimental Study Editor*, Copyright 1995 by the American Academy of Otolaryngology-Head and Neck Surgery Foundation, Inc., pp. 707-713.

K. Whang, Ph.D., "Engineering Bone Regeneration with Bioabsorbable Scaffolds with Novel Microarchitecture," *Tissue Engineering*, vol. 5, No. 1, 1999, *Mary Ann Liebert, Inc.*, pp. 35-53.

\* cited by examiner

TISSUE SUPPORT STRUCTURE

REFERENCE TO PRIORITY DOCUMENT

The present application claims the benefit under 35 U.S.C. 120 of the filing date of U.S. Provisional Application No. 60/652,924, which was filed on Feb. 14, 2005. The contents of U.S. Provisional Application No. 60/652,924 are incorporated by reference as part of this application.

BACKGROUND

The present disclosure relates to tissue support structures, such as tissue scaffolds. For example, the disclosure relates to curved minimal surface tissue scaffolds.

Millions of surgical procedures requiring tissue substitutes to repair or replace malfunctioning tissues are performed worldwide every year. The ever widening gap between the demand and supply of transplant tissues has resulted in seeking natural and biomimetic solutions to address tissue deficiency problems. Autografting, allografting, synthetic prosthetic application, and tissue engineering techniques represent current options for these clinical needs.

Autografting involves harvesting a tissue from one location in the patient and transplanting it to another part of the same patient. Though autologous grafts typically produce the best clinical results, primarily due to minimal rejection, they have several associated problems including procurement morbidity, additional surgical cost for the harvesting procedure, and infection and pain at the harvesting site.

Allografts involve harvesting tissue or organs from a donor and then transplanting it to the patient. Minor immunogenic rejection, risk of disease transmission, and shortage of donors severely limits allografts.

Tissue engineering involves regenerating damaged or malfunctioning organs using cells, biomolecules, and synthetic or natural scaffolds. Tissue engineering involves regenerating damaged or malfunctioning organs from the recipient's own cells. The cells are placed in a tissue culture where they multiply. Once enough number of cells are produced the cells are embedded on a carrier material, scaffold, that is ultimately implanted at the desired site. Since many isolated cell populations can be expanded in vitro using cell culture techniques, only a small number of healthy cells is necessary to prepare such implants. On implantation and integration, blood vessels attach themselves to the new tissue, the scaffold dissolves, and the newly grown tissue eventually blends in with its surroundings. This technology has been effectively used to create various tissue analogs including skin, cartilage, bone, liver, nerve, and vessels.

In spite of the projected benefits of engineered tissues, the percentage share of tissue engineered grafts has not increased tremendously. This is partly due to existing technical hurdles.

SUMMARY

Techniques for generating tissue support structures for promoting efficient cell growth are disclosed.

In one aspect, a tissue support structure is generated by determining a curved minimal surface shape as a template for the tissue support structure; obtaining data indicative of the determined curved minimal surface shape; and generating the tissue support structure based on the data. The data can be exported to a rapid prototyping system to generate a plurality of tissue support structures.

Implementations can include one or more of the following features. The data indicative of the shape can be exported to a solid freeform fabrication to generate a plurality of tissue support structures. A tissue support structure can be generated by creating a pore sub-space and a non-pore sub-space divided by a non-intersecting two-sided surface. The curved minimal surface shape can be determined by selecting a fundamental region and deforming for surface minimality a plane in the fundamental region to obtain a patch. The patch can be tessellated to generate a unit cell having a curved minimal surface, and the unit cell can be further tessellated to generate a monolithic scaffold including repeated unit cells having a curved minimal surface. The curved minimal surface can be a triply periodic Schwartz minimal surface. The patch can be a discrete patch represented by a variable number of triangles. A number of characteristics of a scaffold can be modulated including porosity and the mechanical strength. The porosity can be modulated based on a scale factor, to a value higher than fifty percent. The mechanical strength can be modulated based on a non-zero constant mean curvature. Further, the tissue support structure can be generated to provide parallel seeding and feeding networks by embedding a constant mean curvature version of a Schwartz unit-cell within an optimally evolved Schwartz unit-cell.

These aspects can be implemented using an apparatus, a method, a system, or any combination of an apparatus, methods, and systems. The details of one or more implementations are set forth in the accompanying drawings and the description below. Further features, aspects, and advantages will become apparent from the description, the drawings, and the claims.

DETAILED DESCRIPTION

Techniques for providing an efficient environment for supporting tissue (e.g., human cells) are disclosed. In one aspect of the techniques, methods and systems for generating constructs that are smooth, monolithic, and have minimal surface area are disclosed. The minimal surface constructs can be used as templates for tissue engineering scaffolds. In another aspect of the techniques, methods and systems for facilitating virtual refinement of stochastic scaffolds to create geometric models that can be created using deterministic processes are disclosed.

Tissue scaffolds perform multiple functions including at least the following: (1) provide timely mechanical support and stability to tissue; (2) define and maintain a 3D space for the formation of a new tissue; (3) guide the development of a new tissue to achieve appropriate functions; and (4) localize and deliver human cells to a specific site in the body upon implantation. In one example of tissue engineering using tissue scaffolds, cells are grown in vitro, then embedded in a scaffold material. The resulting structure can then be implanted into a subject and used as a surrogate for tissue (e.g., an organ surrogate). Once the structure is implanted and integrated, the tissue of the support structure can receive nutrients through the subject's blood supply system. The supporting structure (e.g., the tissue scaffold) can later dissolve, and the tissue can become part of the surrounding tissue.

Tissue scaffolds are generally fabricated from materials having one or more of the following properties. The material can be non-mutagenic, non-antigenic, non-carcinogenic, non-toxic, non-teratogenic, and highly bio-compatible. The material can be one or more of biodegradable, bioresorbable, or bioabsorbable.

Preformed structural scaffolds are formed from structural elements such as pores, fibers or membranes. These elements are ordered according to stochastic, fractal or periodic principles and can also be manufactured reproducibly using rapid prototyping approaches like Solid Freeform Fabrication (SFF).

Figure 1:
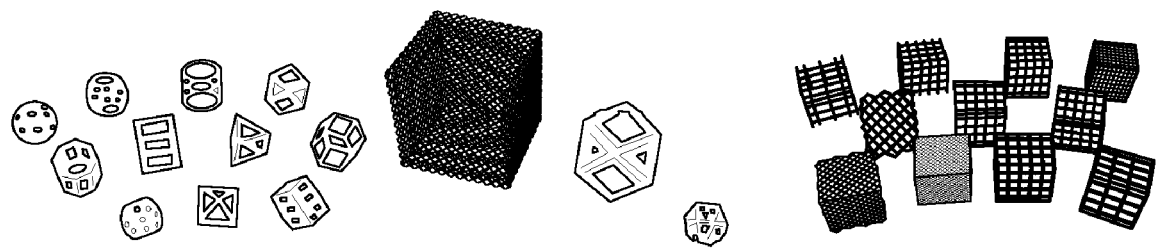
FIG. 1 shows examples of conventional scaffolds based on straight edges with sharp turns.

SFF techniques are computerized fabrication techniques that can rapidly produce complex three-dimensional objects or models using data generated by computer aided design (CAD) systems, medical imaging modalities and digitizers. Existing methods for producing scaffolds using SFF are based on tessellations of unit cells or building blocks of scaffolds derived from Boolean intersections of geometric primitives such as a sphere and a cylinder. FIG. 1 shows some examples of scaffolds created by existing methods. Resultant scaffolds can not provide an efficient environment for tissue engineering and suffer from bulk degradation of scaffold material.

The aggregate of cells, foam/extracellular matrix, typically have cells separated by curved partitions that create space between the partitions. According to one aspect of the techniques, a tissue support structure that provides a better environment for cell growth by utilizing the geometry that best mimic this space is generated. A tissue support structure can be described as having a pore sub-space and a non-pore sub-space, divided by a non-intersecting two-sided surface. The pore subs-space and the non-pore subspace need not necessarily be equal.

Figure 2:
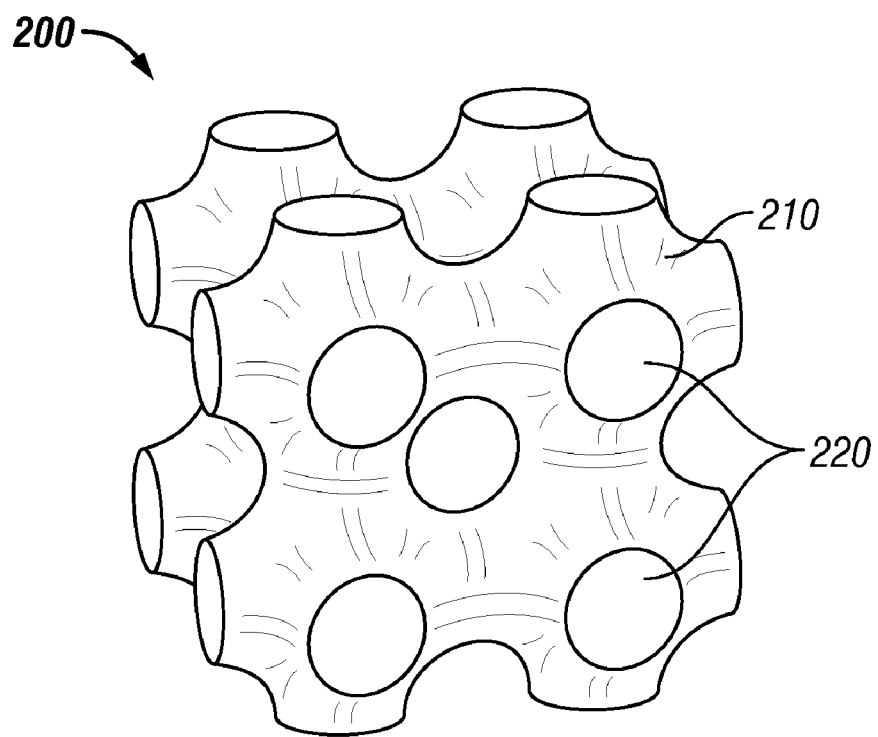
FIG. 2 is a three-dimensional representation of a tessellation of a minimal surface-based unit cell.
Figure 3:
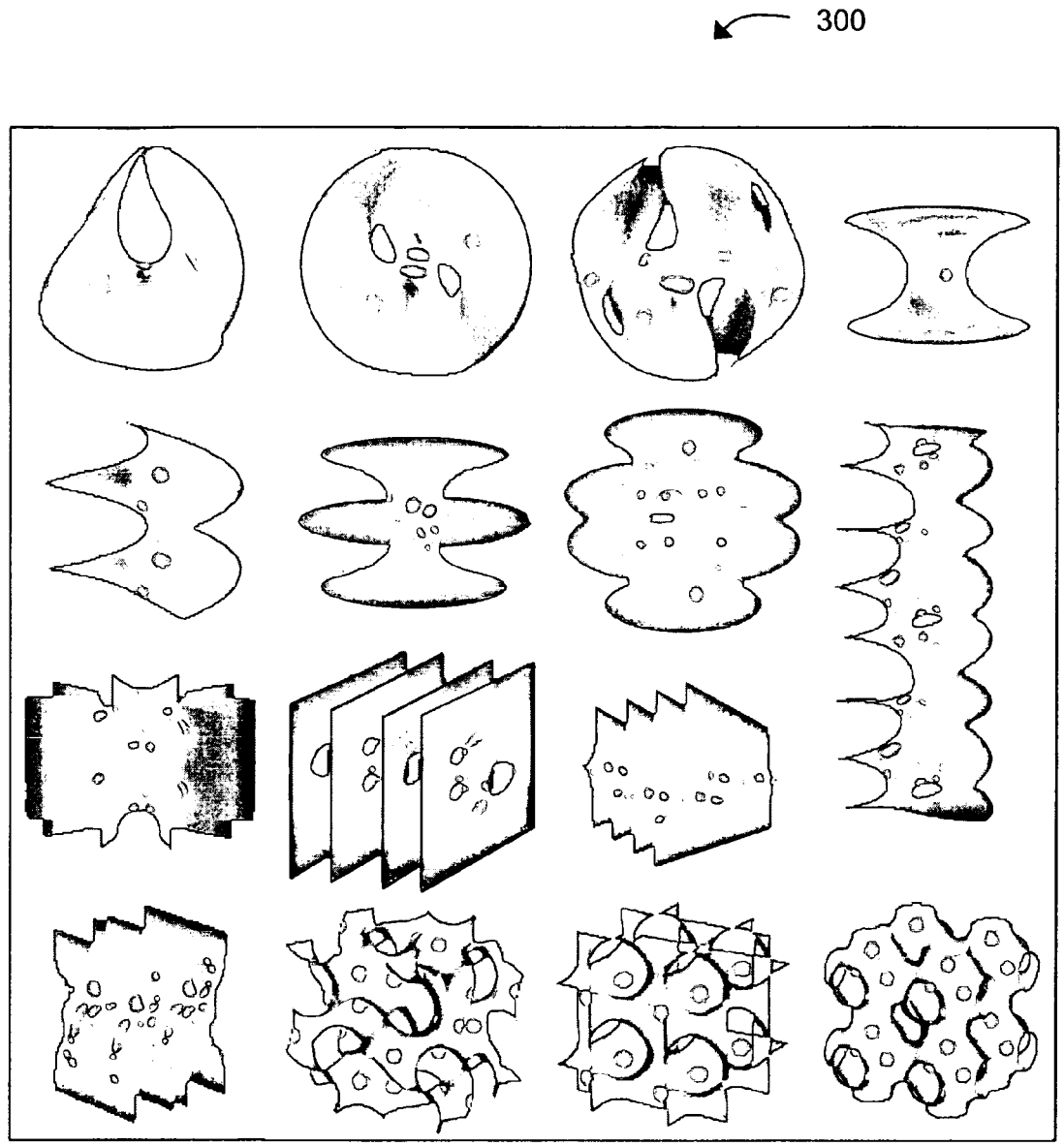
FIG. 3 shows examples of curved minimal surfaces.

In some implementations, the support structure comprises a repeated unit cell having a smooth surface bounded by one or more pore boundaries. FIG. 2 illustrates an example of a support structure 200 with unit cells having smooth surfaces 210 bounded by one or more pore boundaries 220. Surface 210 can be generally smooth and monolithic. Surface 210 can further be a minimal surface. A minimal surface is a surface having a mean curvature (H) of zero everywhere. FIG. 3 shows a number of examples of minimal surfaces 300. In some implementations, the minimal surface is the Schwartz minimal surface (SMS). SMS is triply periodic with translation symmetries in three independent directions and without any self intersections. SMS stems from the following simple but powerful recursive rules used to construct this periodic surface. If part of the boundary of a minimal surface is a straight line, then the reflection across the line, when added to the original surface, makes another minimal surface. If a minimal surface meets a plane at right angles, then the mirror images of the plane, when added to the original surface, also makes a minimal surface. Surface 210 can be a surface that can be described as having a continuous first derivative of the surface function; that is, surface 210 does not have sharp edges or corners except at the pore boundary 220.

Minimal Surface Based Scaffold Fabrication

Figure 4:
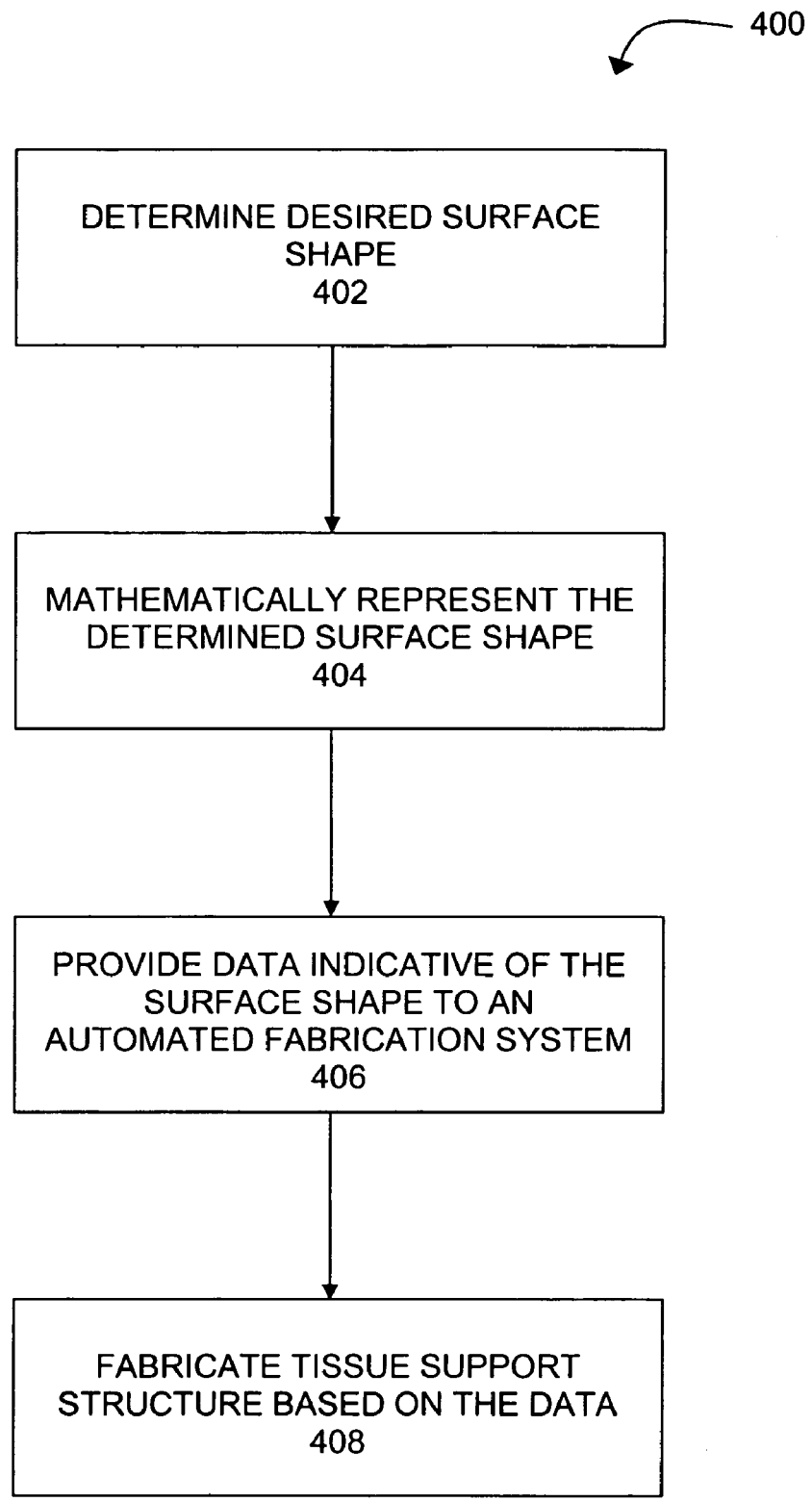
FIG. 4 is a flow chart of a process for generating a curved minimal surface tissue support structure.

Tissue support structures such as those described herein can provide an efficient environment for cell growth. FIG. 4 is a flow chart describing a process 400 for fabricating tissue support structures according to the techniques disclosed herein. A desired surface shape of a triply periodic minimal surface to be used as a template for tissue engineering scaffold can be determined at 402. In determining a surface shape, factors described above such as a particular minimal surface and a particular pore size, for example, are taken into account. In some implementations, other factors are also considered and incorporated into the determination process, at 402, including mechanical strength and durataxicity (dynamic modulation of substrate strength). The determined surface shape can be mathematically represented at 404. In some implementations, a surface function can be generated numerically and/or using a functional representation. Data indicative of the surface shape can be provided to an automated fabrication system, such as a SFF system at 406. A tissue support structure can be fabricated based on the data indicative of the surface shape at 408.

SMS Fabrication

In some implementations, the surface shape determined and generated is a SMS. A SMS can be constructed as a surface defined by a function of Equation (1).

$$\cos(x)+\cos(y)=0 \qquad (1)$$

Alternatively, the SMS can be constructed using a surface, usually a plane, embedded within a tetrahedron and iteratively deforming the primitive shape by minimizing the surface area. The unit cell can be constructed by tessellating the evolved surface patch using the rules mentioned above. Further tessellation of the unit cell establishes the required matrix.

Figure 5A:
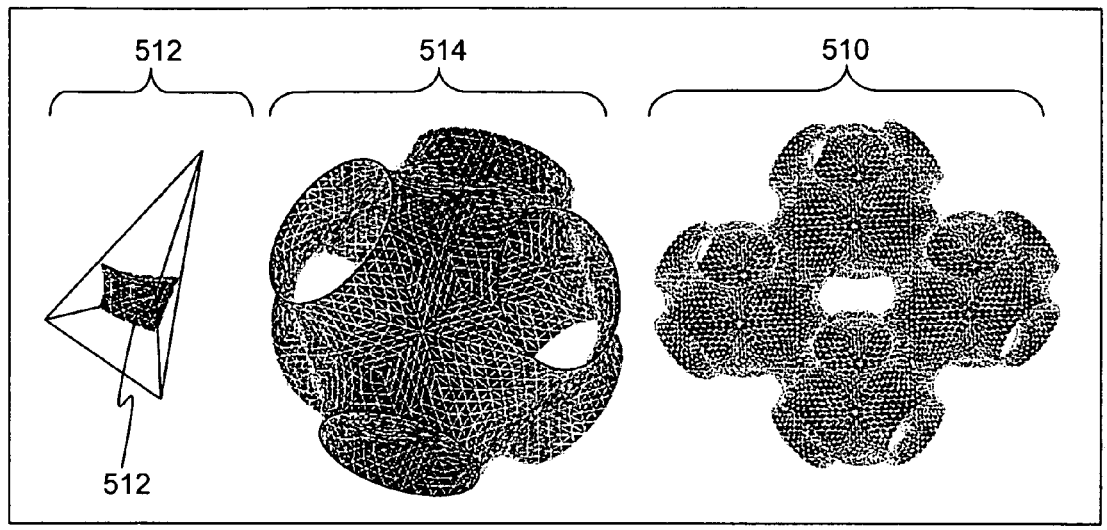
FIG. 5A is an example of a Schwartz minimal surface unit cell and its tessellation.

FIG. 5A describes the progression of creating a SMS scaffold 510 having smooth surfaces according to some implementations. A tetrahedron 512 (⅛ of a cube) is selected as a fundamental region. A plain in the fundamental region is deformed for surface minimality to produce a patch 512. The patch 512 is tessellated using the SMS rule according to techniques described above to produce a smooth unit cell 514. Further tessellation of the unit cell 514 yields a monolithic scaffold 510. The minimal surface patch 512 is a discrete patch represented by triangles whose count can be budgeted using progressive refinement. The monolithic scaffold 510 can be readily exported in STL format for further rapid prototyping using SFF techniques.

Figure 5B:
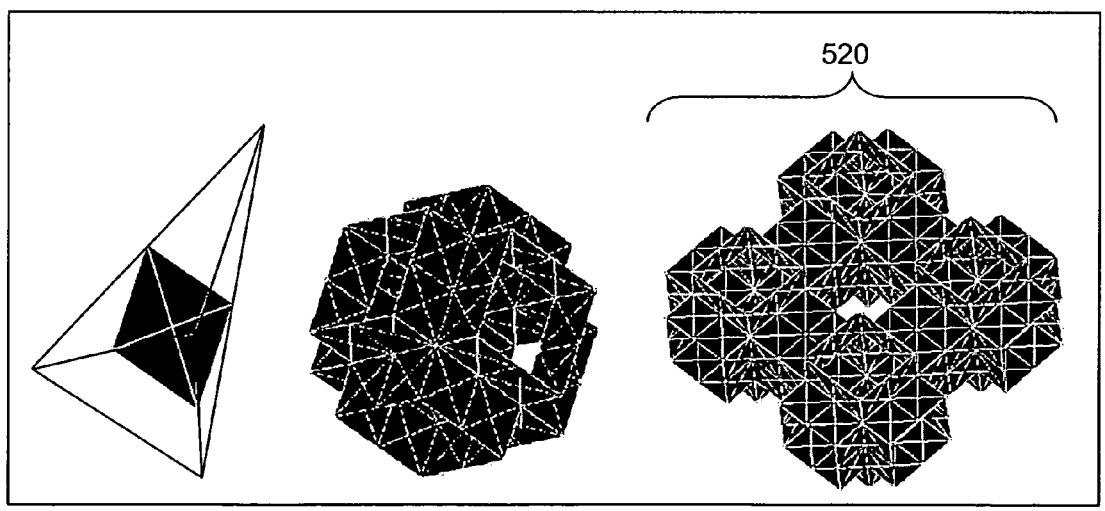
FIG. 5B is an example of a conventional cubic scaffold.

Compare the SMS scaffold to the typical scaffold 520 created using existing methods. FIG. 5B illustrates the progression of creation of a scaffold using typical tessellation process. The resultant scaffold 520 comprises non-smooth surfaces having sharp edges and corners. Such typical scaffold 520 is inefficient in promoting cell growth.

Systems for Fabricating Minimal Surface Based Scaffold

Figure 6A:
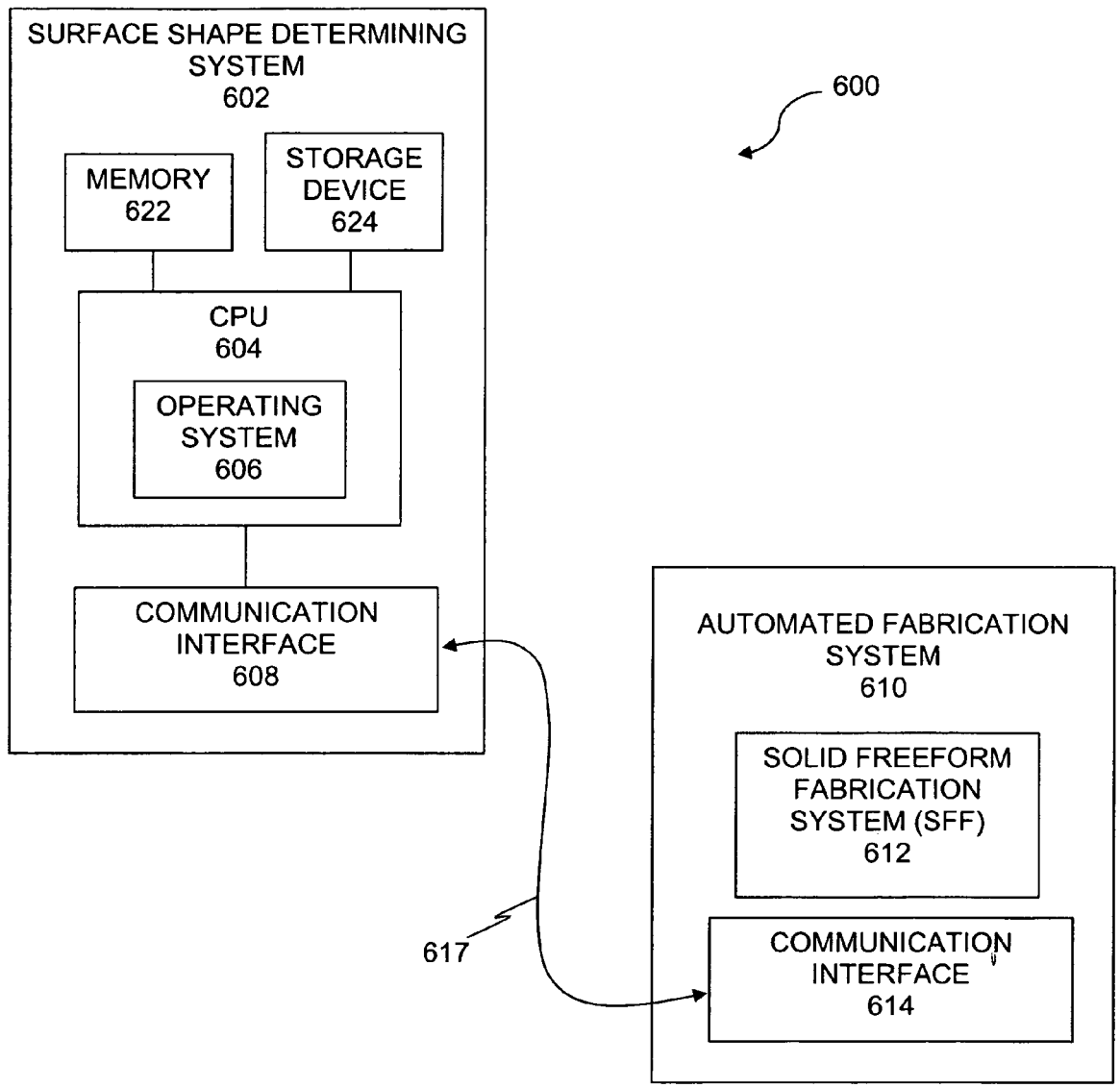
FIGS. 6A-B are functional diagrams of a system for generating a curved minimal surface tissue support structure.
Figure 6B:
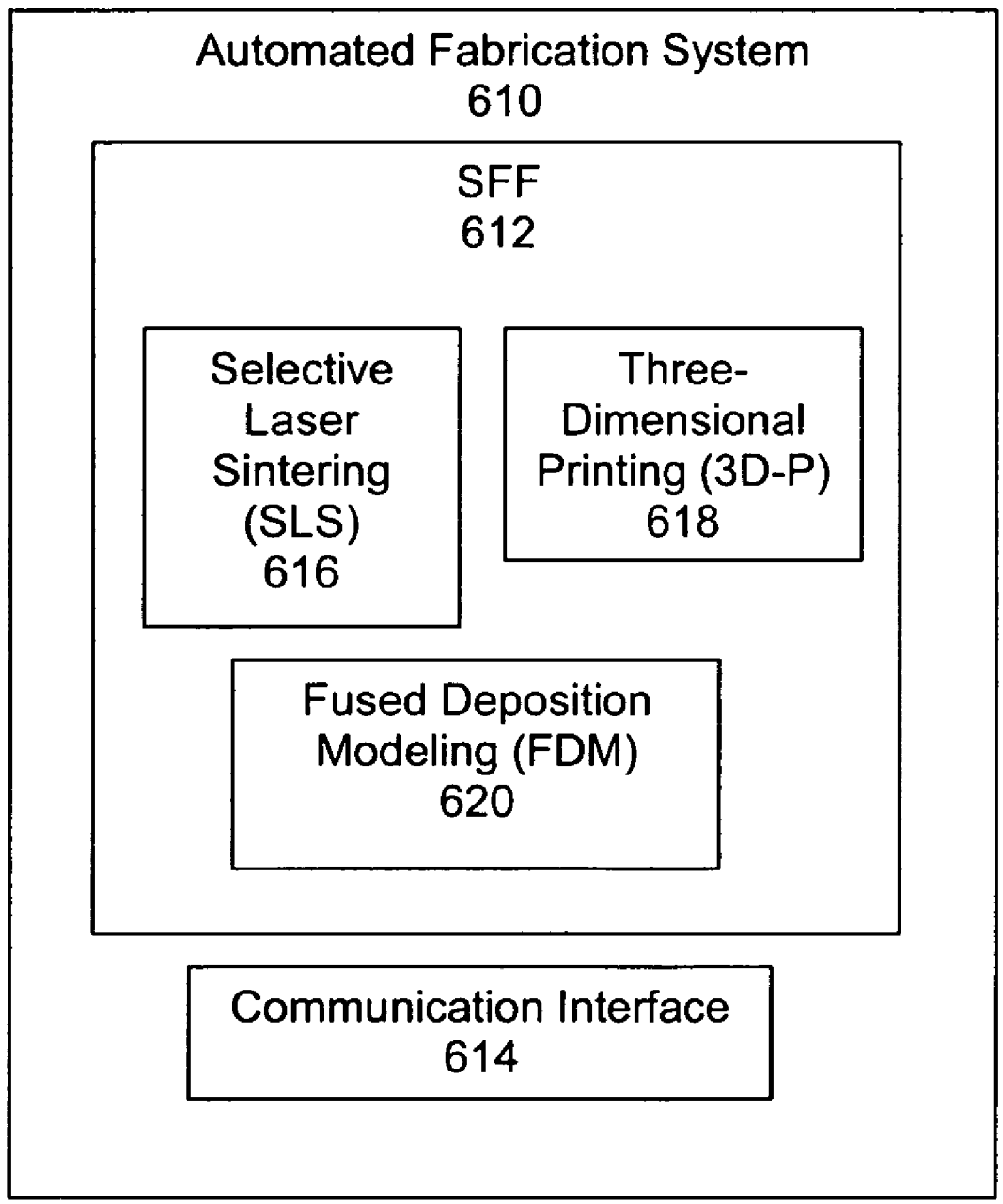

FIG. 6A-B are functional block diagrams describing an automated system 600 for fabricating the tissue structures according to the techniques disclosed herein. The automated system 600 can include a surface shape determining system 602 and an automated fabrication system 610. The surface shape determining system 602 can be implemented as a computer system. The computer system can include at least a central processing unit (CPU) 604, an operating system 606, a communication interface 608, a memory 622 and a storage device 624. The memory 622 can include a volatile RAM-based memory devices such as RAM, DRAM, SDRAM, DDRAM, and other similar devices. The storage device 624 can include a non-volatile storage device such as ROM, CD-ROM, Flash ROM, CompactFlash, and magnetic disk devices. Other components not shown such as input/output devices can readily be implemented on either or both of the surface shape determining system 602 and the automated fabrication system 610.

The automated fabrication system 610 can be implemented as a SFF system. FIG. 6B describes some of the possible types of SFF systems available such as selective laser sintering technique (SLS) 616, three-dimensional printing (3D-P) technique 618, and fused deposition modeling (FDM) 620. The SLS technique 616 utilizes a $CO_2$ laser bean to selectively sinter polymer or composite (polymer/ceramic, multiphase metal) powders to form material layers. The 3D-P technique uses ink jet printing technology for processing powder materials. The 3D-P technique allows a wide variety of powder materials including polymers, metals, and ceramics to be processed. The FDM technique relies on the concept of melt extrusion to deposit a parallel series of material roads that form a material layer. In some implementation, other SFF techniques suitable for fabricating the efficient tissue structures as described herein can be implemented.

The surface shape determining system 602 is connected to the automated fabrication system 610 through a communication link 617. The communication link 617 is a bi-directional communication link between the surface shape determining system 602 and the automated fabrication system 610. In some implementations, the communication link 617 is a physical cable or wire link compatible with typical data communication standards including IEEE 1394 (FireWire) connection, Universal Serial Bus (USB) connection, or other serial or parallel data connections. The communication link 617 typically physically connects to a communication interface 614 on the automated fabrication system 610 and a communication interface 608 on the surface shape determining system 602. The communication interfaces 608 and 614 on the surface shape determining system 602 and the automated fabrication system 610 are compatible with one of the data communication standards (e.g. FireWire or USB) mentioned above.

In some implementations, a connection can alternatively be accomplished using a wireless communication link (e.g., Bluetooth, infrared, or other wireless communication) between the automated fabrication system 610 and the surface shape determining system 602.

Figure 7:
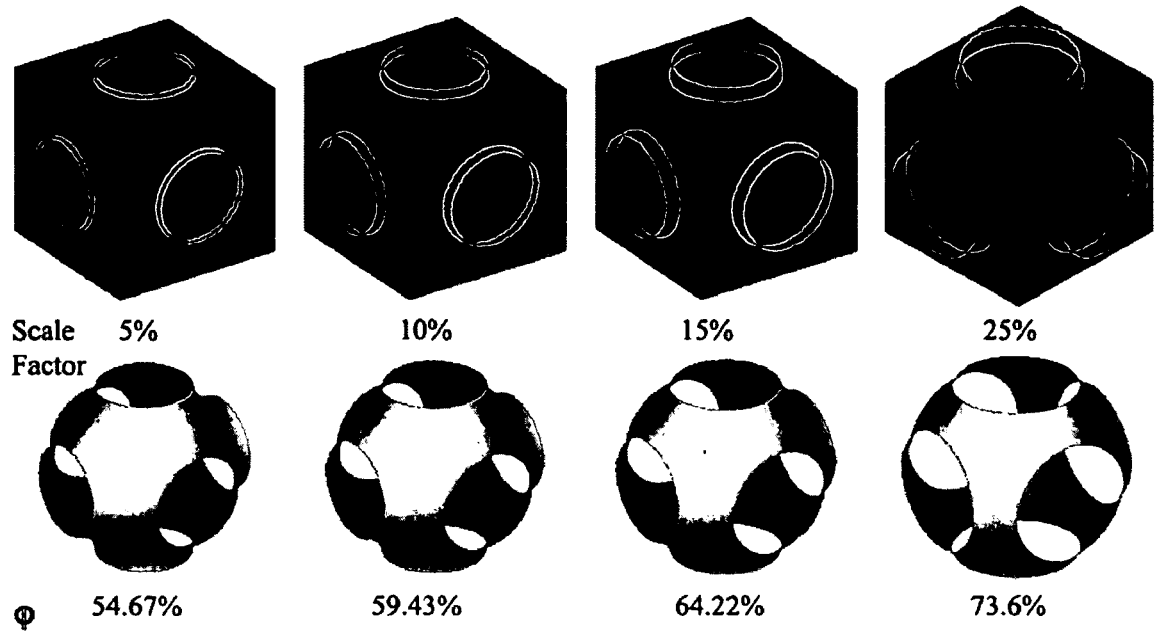
FIG. 7 illustrates a process of modulating porosity.

Using the systems and techniques herein, many different porosity values can be achieved. In some existing systems, the maximum porosity for a monolithic structure can be about fifty percent. For example, the Schwartz minimal surface has a maximum theoretical void area (porosity) of fifty percent. To minimize the amount of material to be washed out on degradation, and to provide sufficient void space for the cells to proliferate, the porosity should preferably be higher. Systems and techniques herein can be used to produce tissue scaffolds having porosities greater than fifty percent; for example, porosities of about sixty percent or greater. Porosity modulation in P-cells can be achieved by recognizing that any small patch cut from a minimal surface would have the least area of all the surface patches with the same boundary and hence also forms the minimum surface. Since a scaled and clipped minimal surface also results in a minimal surface, unit P-cells can be scaled and subsequently truncated with unit cube to form scaled-truncated P-cells. The porosity of these cells will vary depending on the scaling factor used. FIG. 7 shows the result of this scaled-truncation at multiple scaling factors along with the resultant porosity. The increase in porosity is proportional to the scaling factor.

In some implementations, additional characteristics of the scaffold can be modulated. For example, mechanical strength of the scaffold can be altered to suit the desired environment and/or application. Scaffolds must provide structural support at the site of replacement. In addition to the appropriate porosity, pore size, and shape, the scaffold needs appropriate mechanical strength and stiffness suitable for the environment and/or application in tissue engineering. For example, bone and cartilage tissue engineering applications can require different mechanical strength than soft tissue engineering applications.

Techniques described herein allows for modulation of mechanical strength of the scaffold. Substrate stiffness can be modulated in triply periodic minimal surface (TPMS) based scaffolds by evolving the fundamental patch sub-optimally to a non-zero but constant mean curvature. In some implementations, substrate stiffness can be modeled by varying the C (level set value) in the trigonometric function of Equation (2).

$$\cos(x)+\cos(y)+\cos(z)=C \quad (2)$$

Figure 8:
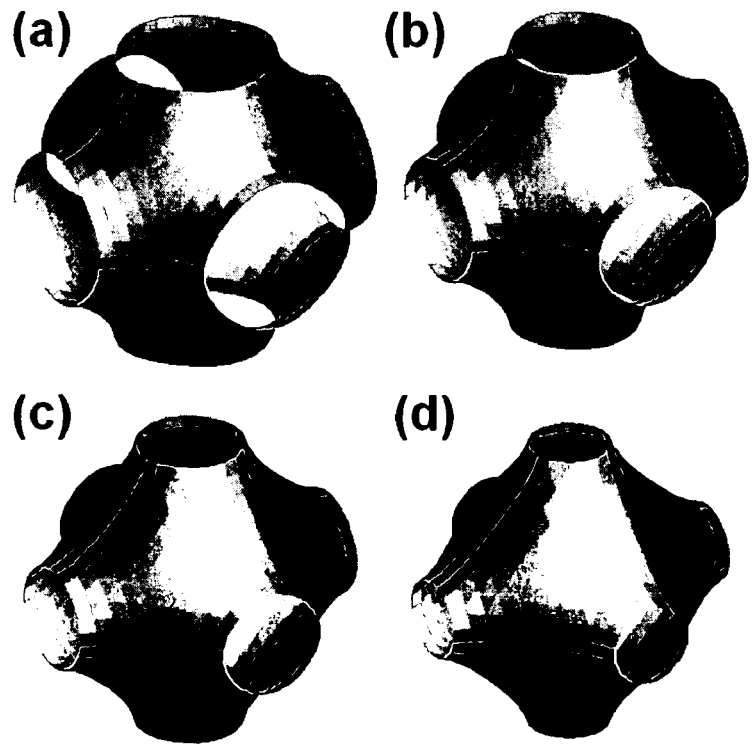
FIG. 8 shows a mosaic of modulated P-Cells.

The resultant Constant Mean Curvature (CMC) surfaces can be at a higher energy state in comparison to the minimal surfaces and hence can be varyingly stiff depending on the constant mean curvature chosen. FIG. 8 shows a mosaic of modulated P-unit cells formed by evolving the fundamental patch at different non-zero mean curvatures.

In some implementations, mechanical strength can be adjusted at least by the selection of the surface shape. The resultant unit cell from different selection of the surface shape can affect overall mechanical strength of the scaffold. In addition, pore size and porosity can also be adjusted to modulate mechanical strength to a desired level. Verification of the mechanical strength of the scaffold can be performed by testing for various mechanical properties including modulus of elasticity in bending and compression, and sheer stress.

Some existing structures can have generally smooth surfaces between some pore boundaries, but can not be monolithic. For example, some existing structures can be generated using a number of layers, where each layer is fabricated using a form. The form can be produced by making protrusions in sheet metal and punching holes through the protrusions to define pore surfaces. Although some local regions of the resulting surface are smooth, because such structures are not monolithic, there can be non-smooth or otherwise inefficient regions where the layers are joined to make the structure.

In various implementations, a tissue support structure is curved and substantially monolithic structure comprising repeated cells, where each cell has a smooth surface function bounded by a pore boundary. The surface function can be represented numerically. However, the surface function need not be functionally representable.

In some implementations, the smooth surface function is a minimal surface function, such as a Schwartz minimal surface function or other minimal surface function.

In some implementations, the tissue support structure can be a monolithic structure having smooth surface representation, and further having a porosity greater than available porosities for monolithic structures (e.g., greater than sixty percent).

Figure 9:
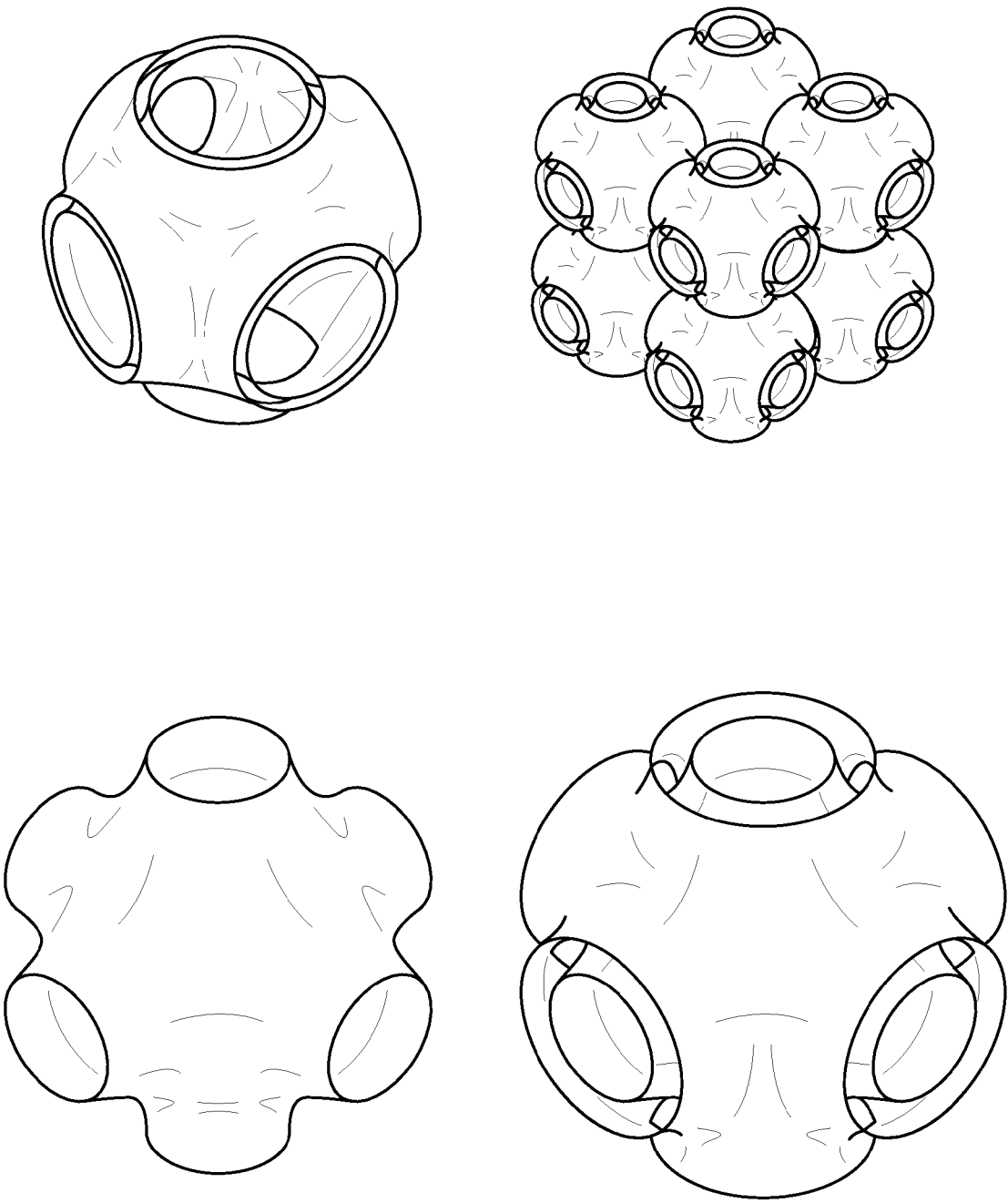
FIG. 9 illustrates a configuration for generating parallel seeding and feeding networks.

The techniques described herein can also be implemented to provide parallel seeding and feeding networks. By embedding a CMC version of the Schwartz unit-cell within the optimally (fully) evolved Schwartz unit-cell parallel, coterminous seeding and feeding networks can be created. FIG. 9 shows such a configuration. Using biphasic materials on such a configuration, the outer shell can be fabricated using stronger materials to provide the needed mechanical strength and the inner shell can be fabricated using softer materials in which nutrients and growth factors can be encapsulated for timed diffusion. Such a strategy can guarantee the much needed nutrient supply for the migrating cells throughout the scaffold geometry.

Virtual Refinement of Stochastic Scaffolds

According to another aspect of the techniques, methods and systems for facilitating virtual refinement of stochastic scaffolds are implemented to allow for repeatable fabrication of tissue support structures. Generation of specific tissues using tissue scaffolds depends on various contributing factors such as pore size, porosity, pore shape, pore interconnectivity, effective scaffold permeability, tortuosity, scaffold stiffness, material, and surface chemistry of scaffolds. Quantitative analysis of these factors is needed to validate the fabrication process and characterize the resultant scaffolds. Such quantitative analysis of scaffolds can facilitate approval by a regulatory agency, such as the United States Food and Drug Agency. Virtual refinement of stochastic scaffolds facilitates fabrication of a plurality of tissue support structures as described above. In addition, the resulting structures can be substantially similar, allowing for sample-from-a-batch characterization and quantitation in a non-destructive manner.

In some existing systems, SFF is used to form tissue scaffolds. The resulting structures can be substantially similar (and thus reproducible and sample-from-a-batch characterizable). However, as noted above, those structures are generally inefficient for promoting efficient cell growth.

In some existing systems, tissue support structures are formed in a non-reproducible manner. That is, in techniques such as phase separation, solvent casting, and the like, porous structures can be formed that are not repeated structures, but rather stochastically ordered. When a plurality of structures are formed, each of the structures is different. These techniques can be referred to as "handcraft" techniques, since the produced structures are effectively "one of a kind" structures. That is, the resulting structures are generally not reproducible using the same technique a plurality of times. Although these structures are not reproducible, they can have desirable characteristics. For example, the structures can be smooth, monolithic structures, efficient for cell growth.

Figure 10A:
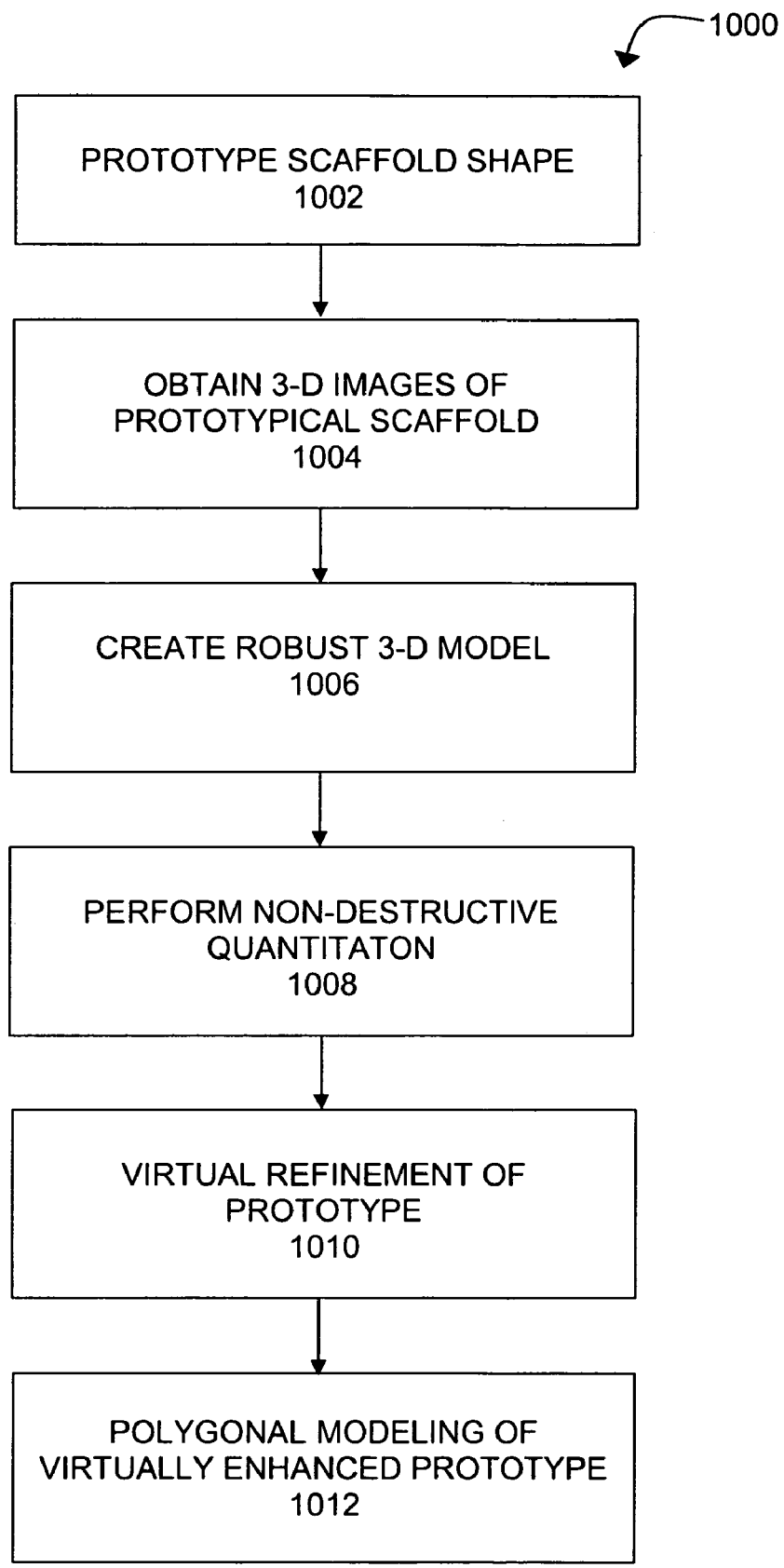
FIGS. 10A-B are flow charts for generating a plurality of substantially similar handcraft scaffolds.

In some implementations, a plurality of structures having substantially similar properties can be fabricated based on a handcraft structure. FIG. 10A is a flow chart describing a process 1000 for forming a plurality of substantially similar handcraft structures. A prototypical handcraft structure is formed at 702 by using traditional techniques. The handcraft structure can have substantially smooth porous structures, which promote efficient cell growth. Three-dimensional imaging of the resulting structure is performed at 1004. MicroCT and/or microMR could be used to obtain quantitative three-dimensional images of the structure.

At 1006, robust three-dimensional modeling of the porous/nonporous network is performed. Accurate description of the porous/non-porous network is a consideration lacking in existing techniques. The microCT/microMR images obtained at 1004 are segmented into polymeric and porous space. Such segmentation is central to the outcome of the subsequent structural and morphometric analysis. Segmentation is performed using intensity based thresholding. In some implementations, different thresholding techniques can be implemented and chosen based on a determined suitability for the given data. Optimal porous/non-porous network can be selected automatically from among a large number of competing results using a blind validation approach.

At 1008, non-destructive quantitation of the porous architecture is performed. A non-destructive quantitation allows for computation of the metrological measures including but not limited to form, position, geometric and mechanical characteristics. Form measures include pore size, porosity, strut width, and roughness. Position measures include interconnectivity, permeability and tortuosity. Geometric measures include pore shape, pore-neck morphology, etc. These metrological measures can be obtained using suitable established techniques.

At 1010, virtual refinement of the prototypical scaffold is performed. By incorporating modeling and visualization techniques, the scaffold architecture can be virtually refined so as to optimize structural and mechanical properties of the scaffold. Such virtual refinement can significantly enhance the architecture of handcrafted scaffolds. Interrogative visualization which involves concurrent rapid computation of relevant metrological measures like porosity, connectivity, tortuosity, and mechanical stability in addition to the computation intensive visualization can be used to interpret, alter and optimize the network topology.

At 1012, polygonal modeling of the virtually enhanced prototype is performed. The optimized scaffold architecture resulting from the virtual refinement process can be polygonized and used as an input model for rapid prototyping. Therefore, structurally enhanced handcrafted scaffolds can be repeatedly and rapidly fabricated using rapid prototyping techniques such as SFF. The ability to implement rapid prototyping in fabricating handcraft scaffolds can facilitate approval from regulatory agencies such as FDA by satisfying the "good manufacturing practices" requirement.

Figure 10B:
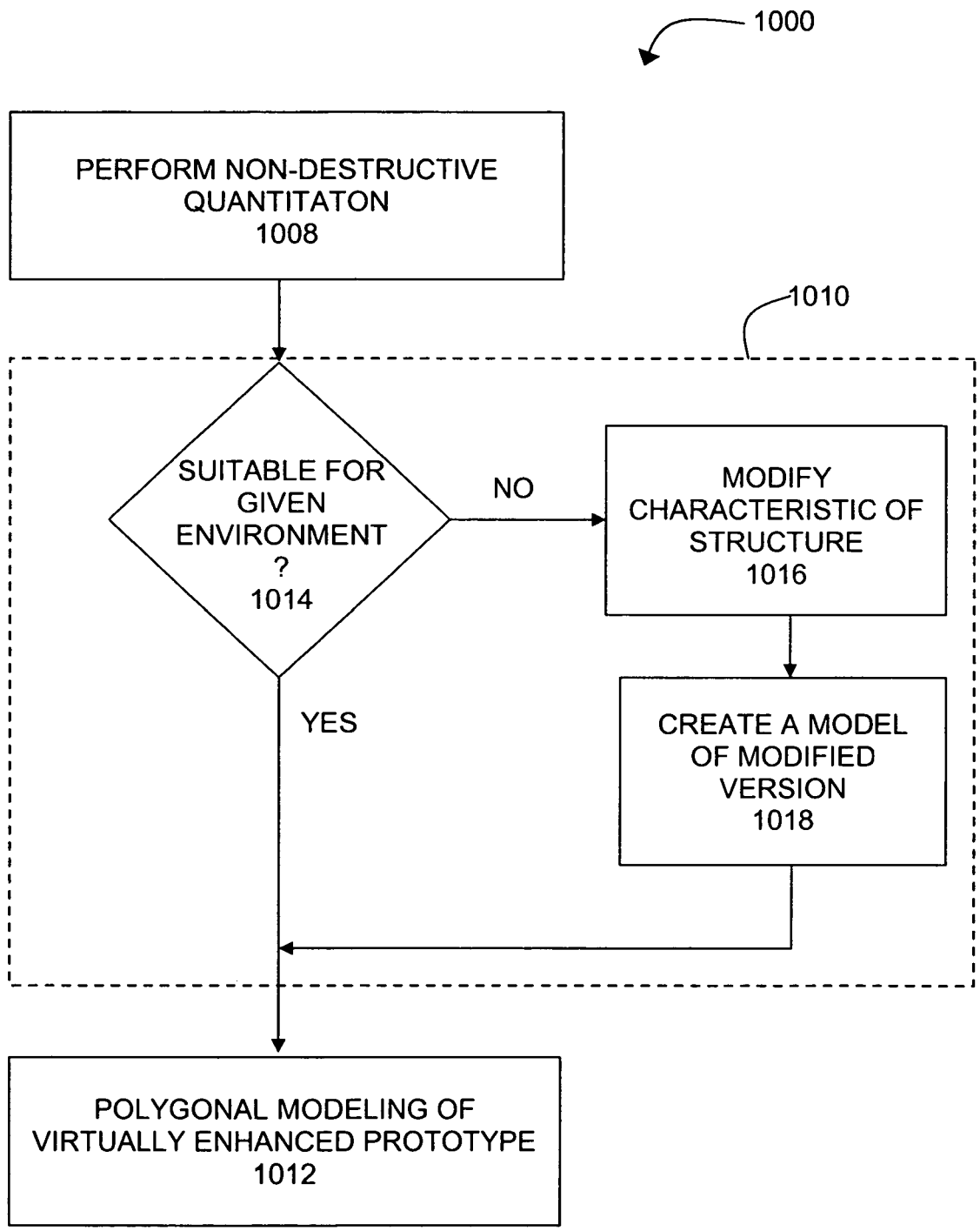

In some implementations, the virtual refinement process at 1010 can include the following implementations as described in FIG. 10B. The characterized prototypical scaffold is reviewed, at 1014, to determine if the scaffold is suitable for a given environment and/or application. If the structure is suitable for a given environment and/or application, a numerical model of the structure can be used to fabricate a plurality of substantially similar structures using rapid prototyping techniques at 1012. A repeatable technique such as SFF can be implemented to fabricate multiple, substantially similar structures.

In some implementations, data indicative of the quantified structure can be used to create a model of a structure having improved characteristics. For example, the resulting handcraft structure can have a minimum pore size smaller than an efficient pore size for a particular use of the structure. In such implementations, a decision is made that the structure is not suitable for the given environment at 1014. The data indicative of the quantified structure can be modified at 1016 so that the minimum pore size is increased. At 1018, a numerical model for a tissue support structure is generated based on a modified version of the handcraft structure incorporating the increased pore size. A tissue structure can then be created based on the modified model using repeatable techniques such as SFF at 1012.

In some implementation, other characteristics of the scaffold can be modulated including mechanical strength.

Thus, the systems and techniques described above can be used to produce a plurality of substantially similar tissue structures (e.g., the structures may have slight differences due to the manufacturing process). The substantially similar tissue structures can be either similar to a handcraft tissue structure, or can be a modified version of a handcraft tissue structure (e.g., a structure with a stochastic porous architecture exhibiting one or more desired characteristics such as a minimum pore size, minimum strength, etc.)

The resulting structure is different than current SFF structures, which are generally produced from Boolean intersections of geometric primitives like a sphere and cylinder, and are repeated versions of a base cell rather than a stochastic porous architecture. A plurality of substantially similar structures can be characterized by a curved monolithic surface bounded by pore boundaries. However, the structure does not necessarily comprise repeated cells.

Figure 11:
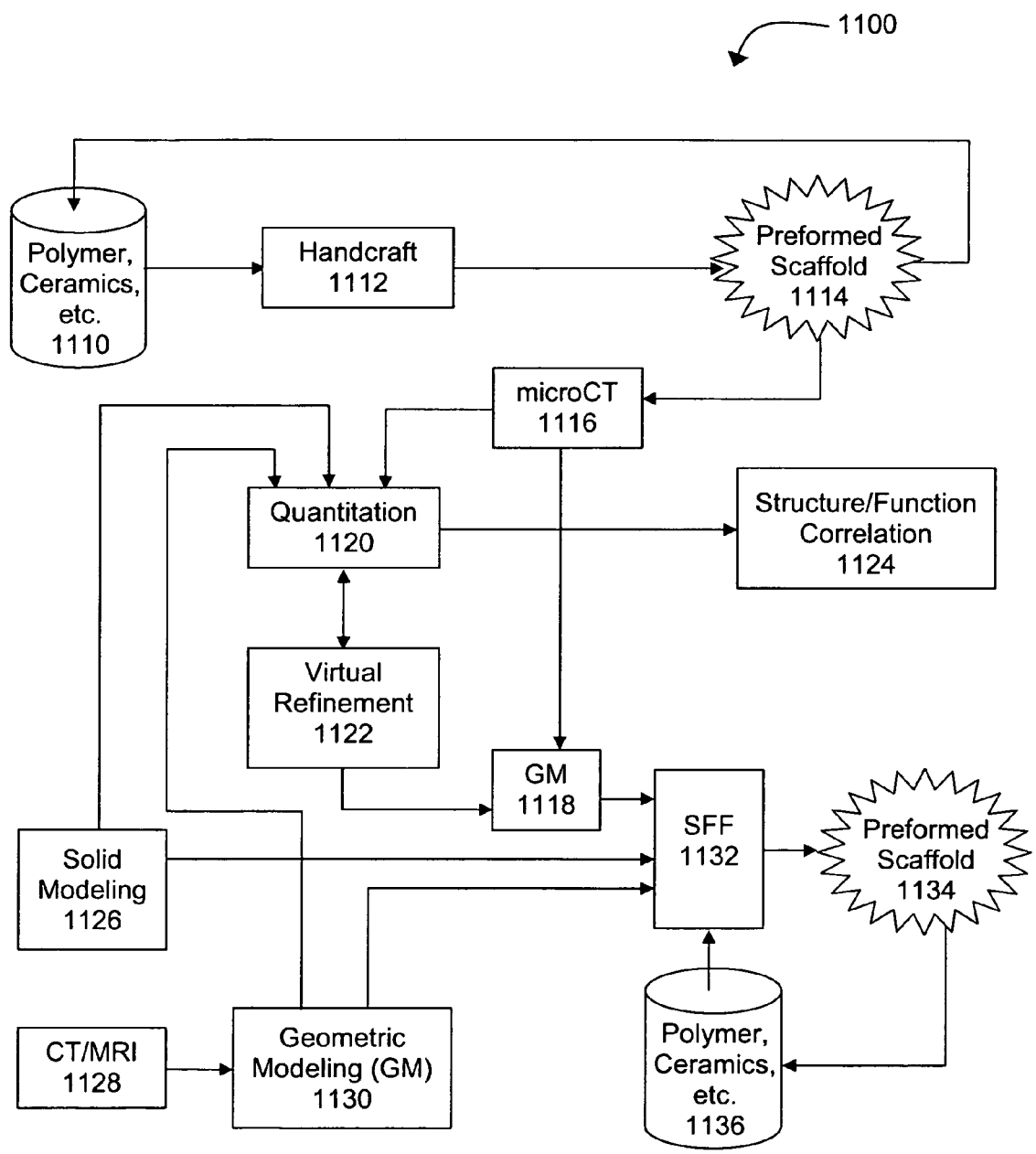
FIG. 11 is a fabrication pipeline for creating multiple scaffolds of substantially similar handcraft scaffolds.

In some implementations, rapid prototyping of handcraft scaffold structures is accomplished by implementing a fabrication pipeline 1100 as described in FIG. 11. The pipeline 1100 includes functional components that can be implemented to perform the process described in FIGS. 10A-B. For example, a preformed scaffold module 1114 fabricates a preformed scaffold using traditional handcraft scaffold fabrication techniques 1112 from biocompatible materials 1110 such as a polymer, ceramic, and other suitable synthetic materials. Traditional fabrication techniques can include fiber bonding, phase separation, solvent casting, particulate leaching, membrane laminating, melt molding, gas foaming, high pressure processing, hydrocarbon templating, and freeze drying. Three dimensional images of the preformed scaffold 1114 is captured using suitable imaging technique such as microCT 1116. The images captured using microCT 1116 can be used to perform non-destructive quantitation 1120. Such quantitation provides information related to structure/function correlation 1124. Based on the quantitation, a series of virtual refinements can be performed to adjust and tailor a scaffold design as needed. Alternatively, images of human tissue and/or preformed scaffold 1114 are captured using computer-aided tomography (CT) and/or magnetic resonance imaging (MRI) 1128. Further yet, a CAD solid modeling system 1126 can be implemented to create an input model for a rapid prototyping system such as SFF 1132. Images captured 1116, 1128 are used to generate a geometric model 1118, 1130. The data obtained from a geometric model is fed to a SFF system 1132 to rapid prototype multiple, substantially similar scaffolds 1134 using suitable materials 1136 such as ceramics and polymers.

In some implementations, tissue structures (e.g., a plurality of substantially similar tissue structures) are provided as described above. In some implementations, methods for forming tissue support structures are provided such as those described above. In some implementations, the above-described methods can be implemented at least partially in software.

In implementations, the above described techniques and their variations can be implemented as computer software instructions. Such instructions can be stored on one or more machine-readable storage media or devices and are executed by, e.g., one or more computer processors, or cause the machine, to perform the described functions and operations. The machine-readable medium may include a hard disk drive, a flash memory device, a random access memory device such as DRAM and SDRAM, removable storage medium such as CD-ROM and DVD-ROM, a tape, a floppy disk, a CompactFlash memory card, a secure digital (SD) memory card, or some other storage device. In some implementations, the computer executable code may include multiple portions or modules, with each portion designed to perform a specific function described in connection with FIGS. 4, 10A-B and 11 above. In some implementations, the techniques may be implemented using hardware such as a microprocessor, a microcontroller, an embedded microcontroller with internal memory, or an erasable programmable read only memory (EPROM) encoding computer executable instructions for performing the techniques described in connection with FIGS. 4, 10A-B and 11 above. In other implementations, the techniques may be implemented using a combination of software and hardware.

Processors suitable for the execution of a computer program include, by way of example, both general and special purpose microprocessors, and any one or more processors of any kind of digital computer, including graphics processors, such as a GPU. Generally, the processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of non volatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

A number of implementations have been described. Nevertheless, it will be understood that various modifications can be made without departing from the scope of the disclosure. For example, different types of surfaces can be used.

What is claimed is:

1. A method of fabricating a reproducible tissue support structure, the method comprises: using a non-stochastic, deterministic process to fabricate the reproducible tissue support structure, the non-stochastic deterministic process comprising: determining a smooth and monolithic curved minimal surface shape as a template for the reproducible tissue support structure, wherein the smooth and monolithic curved minimal surface comprises a surface having a mean curvature of zero bounded by one or more pores, obtaining data indicative of the determined curved minimal surface shape; and fabricating the repeatable and reproducible tissue support structure based on the obtained data, wherein the reproducible tissue support structure comprises repeated unit cells having the curved minimal surface shape which exhibits at least one structural characteristic selected from the group consisting of pore size, mechanical strength, or durataxicity, which are the same structural characteristics exhibited by the surface of the template.

2. The method of claim 1, further comprises fabricating a plurality of tissue support structures using a rapid prototyping technique.

3. The method of claim 2, wherein the rapid prototyping technique is solid freeform fabrication.

4. The method of claim 1, wherein fabricating the tissue support structure comprises creating a pore sub-space and a non-pore sub-space separated by a non-intersecting two-sided surface.

5. The method of claim 1, wherein determining the smooth and monolithic curved minimal surface shape comprises:
   selecting a fundamental region; and
   deforming for surface minimality a plane in the fundamental region to obtain a patch.

6. The method of claim 5, wherein obtaining the data comprises defining the smooth and monolithic curved minimal surface shape using a surface function generated using a numerical model, a functional representation or both.

7. The method of claim 6, wherein fabricating the tissue support structure comprises:
   tessellating the patch to fabricate a unit cell having the smooth and monolithic curved minimal surface; and
   tessellating the unit cell to generate the monolithic scaffold comprising the repeated unit cells having the smooth and monolithic curved minimal surface.

8. The method of claim 7, wherein the smooth and monolithic curved minimal surface is a triply periodic Schwartz minimal surface.

9. The method of claim 7, wherein the patch is a discrete patch represented by a variable number of triangles.

10. The method of claim 1, further comprises modulating a porosity of the tissue support structure based on a scaling factor that changes a size of each pore.

11. The method of claim 10, wherein the porosity is greater than fifty percent.

12. The method of claim 5, further comprises modulating a mechanical strength of the tissue support structure by evolving the patch to a non-zero constant mean curvature.

13. The method of claim 1, further comprises creating parallel seeding and feeding networks by embedding a constant mean curvature version of a Schwartz unit-cell within an optimally evolved Schwartz unit-cell.

* * * * *